(12) United States Patent
Avellanet et al.

(10) Patent No.: US 7,957,819 B1
(45) Date of Patent: Jun. 7, 2011

(54) DISPOSABLE LOW PROFILE TRANSVENOUS ELECTRODE SYSTEM FOR SEQUENTIALLY PACING THE HEART'S RIGHT ATRIUM AND RIGHT VENTRICLE (AV)

(76) Inventors: Frank Avellanet, Westport, CT (US); Eduardo de Marchena, Miami, FL (US)

( * ) Notice: Subject to any disclaimer, the term of this patent is extended or adjusted under 35 U.S.C. 154(b) by 409 days.

(21) Appl. No.: 11/612,690

(22) Filed: Dec. 19, 2006

Related U.S. Application Data

(60) Provisional application No. 60/597,741, filed on Dec. 19, 2005.

(51) Int. Cl.
*A61N 1/05* (2006.01)
(52) U.S. Cl. .................................................. 607/123
(58) Field of Classification Search .................. 607/123, 607/115, 116, 119
See application file for complete search history.

(56) References Cited

U.S. PATENT DOCUMENTS 3,865,118 A * 2/1975 Bures ............................. 607/123
5,871,530 A * 2/1999 Williams et al. ............... 607/122

* cited by examiner

*Primary Examiner* — Eric D. Bertram
(74) *Attorney, Agent, or Firm* — Todd L. Juneau

(57) ABSTRACT

A low profile transvenous electrode system for use in an emergency to sequentially pace both the atrium and ventricle of the heart in a dual chamber mode that includes a plurality of pre-formed, pre-shaped resilient insulated electrical wires bundled together in a tubular, flexible retaining sheath that is used as a guide and delivery system during insertion and removal of the electrode system. When the sheath is retracted, it allows the wires to escape from the sheath and because of their pre-formed shape, each wire having memory, the wires spread out and contact the endocardial surfaces inside the ventricle and atrium chambers. Each of the wires have ball tips to provide high current density and sensitivity.

5 Claims, 1 Drawing Sheet

DISPOSABLE LOW PROFILE TRANSVENOUS ELECTRODE SYSTEM FOR SEQUENTIALLY PACING THE HEART'S RIGHT ATRIUM AND RIGHT VENTRICLE (AV)

BACKGROUND OF THE INVENTION

1. Field of the Invention

This invention relates to the field of pacing and pacemakers for the human heart and, specifically, to emergency pacing required for disorders of cardiac conduction. The present invention relates to an electrode system that is inserted into a human heart for patients either with severe bradycardia or heart block to avoid loss of consciousness or even death, or to prevent such arrhythmias in those at risk.

2. Description of Related Art

Patients that have a medical condition such as severe bradycardia or heart block must have their hearts electrically paced in order to avoid loss of consciousness or even death. Heart block occurs when the electrical stimulation that originates in the SA node, located in the upper chamber of the heart known as the atrium, is unable to propagate to the lower node, named the AV node, to the main pumping chambers of the human heart named the ventricles. This condition is known as disorder of the cardiac conduction system. Heart block frequently develops suddenly without major warning. The net result is a dangerous slowing of the heart rate which leads to decreased, inadequate blood flow to the body, especially to the brain causing dizziness or loss of consciousness and may even cause death.

In the current state of the art, in an emergency, emergency transvenous pacing leads can be inserted into the right ventricle to stimulate the ventricle. This allows for pacing of the ventricles, but results in a loss of atrial ventricular synchrony. The atrium does not contract synchronously prior to the ventricle with "single chamber" ventricular pacing. This anomaly results in a marked reduction of pumping efficiency of the heart. With patients that are in a state of structural heart disease or myocardial infarction, atrial-ventricular synchrony becomes even more essential for adequate blood flow to the body. Thus, even in emergency situations, stimulating the ventricle only with transvenous pacing is less than an optimal solution to the problem.

Although a second lead (electrode) can be inserted into the right atrium to allow atrial-ventricular "dual chamber" pacing in its various forms known to cardiologists, this technique is time consuming and cumbersome to do in an emergency situation. Also, leads are frequently difficult to reliably anchor in the atrium. For these reasons, the practice of emergency atrial-ventricular sequential pacing is not as commonly accepted by the emergency medical communities as it could be, despite the general appreciation of its utility.

The present invention overcomes the problems in the prior art by providing an emergency pacemaker that will pace and sense both atrial and ventricular chambers and provide "dual chamber" control of the heart using a lead that can be safely and easily inserted into the heart in an emergency situation.

"Dual chamber" pacing refers to continuous monitoring of the spontaneous activity of the heart both in the atria and in the ventricles, interpreting the detected events according certain accepted algorithms and providing stimuli to the chambers as needed to maintain a physiologically appropriate rhythm.

SUMMARY OF THE INVENTION

A low profile transvenous electrode system for sequentially pacing both the atrium and ventricle of the heart in the "dual chamber" mode, comprising a plurality of insulated electrical wires bundled together to form at least two in-line sets of leads is disclosed. Both sets of leads are mounted and contained inside a slender, tubular, flexible retaining sheath that serves as a guide and delivery system during insertion and removal of the electrode system. Each of the wires is surrounded individually by electrical insulation. The bundle of insulated wires can be arranged in either a parallel or helical configuration. In order to conform to heart chambers of different sizes, the leads will be produced in different lengths and appropriate distances between the electrodes.

The electrode system is constructed by assembling a plurality of insulated superelastic electrically conductive wires. The insulation material separates each of the wires from each other, but the wires are mounted in a bundle as a single cable-like structure. At the proximal end, the electrodes are connected to an external pacemaker. At the distal end, the individual wires once inserted into the heart will make contact with either atrial or ventricular tissue. The distal ends of the individual wires may include spherical electrode contacts that will make contact with atrial tissue or ventricular tissue.

Each of the wires has memory and is pre-formed in a specific curvature but also is resilient enough to be contained in the sheath prior to being positioned within the heart chambers. Since both sets of leads for the ventricle and the atrium are contained inside a single slender flexible retaining sheath that is the guide and delivery system during insertion and removal of the electrode system, the ventricular electrode or electrodes which can be pacemaker sensors or stimulators are released first after the retaining sheath has been successfully inserted into the right ventricle. At this point, the sheath is retracted allowing the ventricle wire leads to escape from the sheath and because of each wire's pre-formed shape which has memory, spread out to individually contact the endocardial surfaces. The leads expand outwardly, engaging the tissue and chamber wall of the ventricle. If a mechanical parallel wire configuration is chosen in the sheath, the wires can be released and make contact in the same plane. Otherwise, the wires can be staggered within the ventricular chamber. If a helical configuration of the wires is chosen in the sheath, the wires are staggered upon release to cover different points of a chamber wall. Ideal wires for this configuration are disclosed in U.S. Pat. No. 6,137,060 and U.S. Pat. No. 3,699,886.

Continued retraction of the sheath will then allow the escape of the atrial wires and electrodes which also have memory and which, upon escape from the sheath, will proceed outwardly towards the atrial tissue for engagement.

As discussed above, the distal ends of the individual wires may have spherical conductive ball tips to provide high current density and sensitivity. For the physician to effectively introduce the device transvenously, the sheath will have to be extended all the way forward initially such that it covers all the wires with the possible exception of the distal electrodes, which may protrude beyond the sheath during the introduction of the sheath with the conducting leads into the heart. The path of the sheath with the leads during insertion is into the subclavian or jugular vein past the atrium and into the ventricle. Once the electrode system reaches the apex of the right ventricle, the operator begins to pull back slowly on the sheath, thus releasing each wire individually until all necessary contact points are made.

Since each wire is made of a superelastic or memory shape retention material such as Nitinol™, as the sheath is slowly pulled back the wires are released. Each wire will be pre-shaped with the proper orientation so that as the emergency personnel pulls the sheath back, the wire fans outwardly until the wire tips rest against the interior wall of each chamber, thus making electrical contact. The memory in the wire will hold it in place within the chamber. The ball tip ending of each wire as well as the highly flexible chosen material will minimize trauma to the endocardium while allowing a sufficiently large surface area for electrical conduction.

In order for the electrode system within the sheath to freely navigate through the blood vessels, it must have a very smooth surface. Adequate flexibility must be achieved with materials that do not fracture or fail prematurely. The insulation material used to insulate each individual wire will be of the type used in the production of existing pacing leads. Furthermore, the sheath material used will be a thermoplastic elastomer similar to those used in the manufacture of catheters and for added strength it can be braided. The electrode system in accordance with this invention is being designed primarily for emergency temporary use such that the leads described have passive fixation. However, it is possible that the present invention can be utilized as part of a permanently implanted pacemaker system such that the electrode would become embedded in the heart tissue or actively attached to the endocardium by one of many means available for active fixation.

The present invention can be used in emergency rooms, intensive care units, at the bedsides, cardiac catheterization labs, ambulances, battle fields and other emergency settings where patients with heart block or other life threatening arrhythmias may be found.

It is an object of this invention to provide a transvenous electrode system for heart block use in an emergency situation that is low cost, safe and reliable for pacing both the atrium and ventricle chambers of the heart of a patient with a heart block.

It is another object of this invention to provide an emergency heart pacemaker that requires only a small incision to insert the lead that will provide dual chamber (sequential) pacing and sensing for the atrial and ventricles of the heart.

And yet still another object of this invention is to provide an emergency pacemaker that will avoid problems of single chamber ventricular pacing so that the present invention provides for atrial-ventricular synchrony.

In accordance with these and other objects which will become apparent hereinafter, the instant invention will now be described with particular reference to the accompanying drawings.

BRIEF DESCRIPTION OF THE DRAWINGS

The drawing is a schematic view of a cross-section of a human heart, a plurality of electrodes inserted in the ventricle and atrium contacting the walls of the heart chambers and a pacer, all in accordance with the invention.

PREFERRED EMBODIMENT OF THE INVENTION

Figure 1:
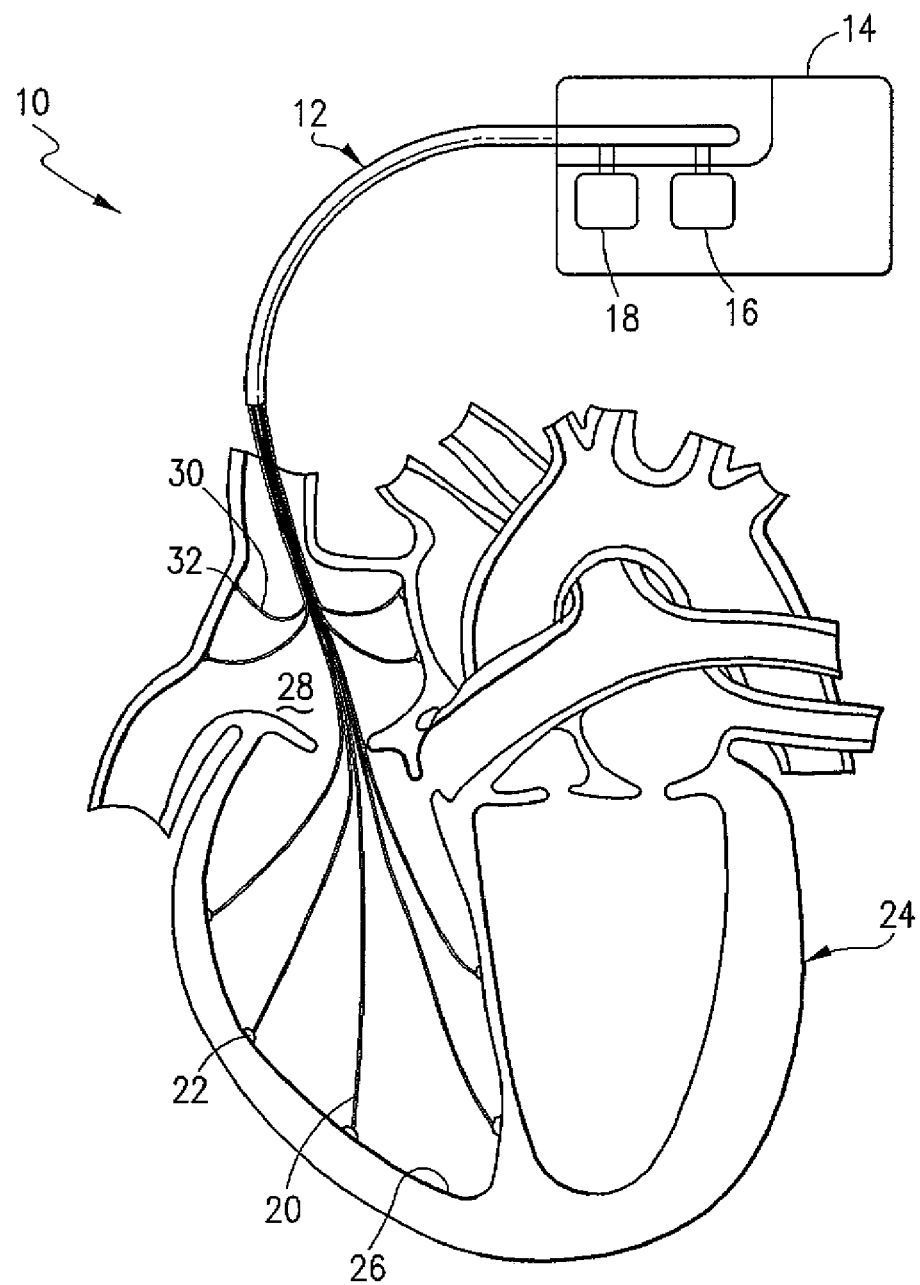

Referring now to the drawing, an external pacemaker 14 is shown connected to a bundle of insulated wire electrical conductors wrapped in a sheath 12. Specifically, the pacemaker 14 as shown is connected to a bundle of ten insulated conductive wires, five wires 20 of which are disposed within the ventricle 26 and four wires 20 of which are disposed in the atrium 28. The wires 20 and 30 are bundled in a sheath 12 that was inserted into the apex of the ventricle 26 and then pulled backward, exposing the five leads 22 which are now contacting the walls of the ventricle 26 due to the retained curved memory of each wire 20. As the sheath 12 is further withdrawn into the atrium 28, four additional electrodes 32 are shown contacting atrial chamber 28 walls in accordance with the present invention.

As shown in the drawing, the invention as disclosed is a low profile transvenous electrode system for sequentially pacing both the atrium and ventricle of the heart in a dual chamber mode. As shown in the drawing, there are a plurality of insulated electrical wires represented as 20 and 30 that are electrical conductors and that are wrapped in electrical insulators. The wires 20 and 30 are bundled together into two separate in-line sets of leads. Each wire 20 and 30 has memory and is resilient. During manufacturing, each wire is pre-formed in a particular curvature and length so that when disposed within a heart chamber, atrium or ventricle, the electrode end of the wire will engage the chamber wall for electrical pulse transfer. Each of the wires 20 in the ventricle could be of different lengths with different shapes so that when the sheath is removed, each wire expands out by memory to have sufficient resiliency in distance to contact the inner wall of the ventricle 26 as shown with the electrode points 22 flush against the ventricle wall. There is be a certain amount of resiliency in each wire 20 holding the wire against the wall during pacing in the position as shown. The four wires 30 used in the atrium are also pre-formed in curvature and length so that when the sheath is removed, wires 30 expand resiliently against the walls of the atrium 28 as shown in the drawing with electrode points 32 disposed at the end of each wire against the wall tissue. The resiliency in each wire will hold the electrodes 32 against the wall of the atrium 28 while pacing.

The external pacemaker 14 provides the electrical pulses for the sequential pacing. The pacemaker 14 has two sequential pulse generators 16 and 18 which are connected to the proximal ends of the wires 20 and 30 for providing the sequential pulses to both the ventricle through wires 20 and to the atrium through wires 30. The external pacemaker itself is conventional in operation.

The leads which are the wire conductors and electrodes are manufactured in different lengths and curved resiliently as discussed above with approximate distances between the electrodes to create a configuration or pattern as shown in the drawing as established inside the ventricle 26 and with a pattern established in the atrium with wires 30. The wires 20 and 30 have memory and with their pre-formed curvatures are resilient enough to be bundled in a small sheath 12 prior to being mounted within the heart chambers. Both sets of wires 20 and 30 are contained inside a single, cylindrical, flexible retaining sheath 12 that is the guide and delivery system during insertion and removal of the electrode system. The ventricular electrodes 22 which can be pacemaker sensors or stimulators are released first after the retaining sheath has been successfully inserted into the right ventricle 26. The sheath 12 is retracted allowing the electrodes 22 and wires 20 to spread out and contact the endocardial surfaces. The wires expand outwardly as the sheath is removed engaging the tissue and chamber wall of the ventricle 26. With a parallel configuration of wires is chosen, the wires can be released and make contact on the same plane within the ventricular chamber or they can be staggered.

The continued retraction of sheath 12 allows the escape of the atrial wires 30 from the sheath which proceed toward the atrial tissue 28 for engagement of the electrodes 32 against the atrial wall.

Once the electrodes have been predisposed within the ventricular chamber and the atrium, pacing can begin sequentially pacing both the atrium and ventricle in a dual chamber mode providing an emergency pacemaker that will pace and sense both atrial and ventricular chambers and provide dual chamber control of the heart. The dual chamber pacing refers to continuous monitoring of the spontaneous activity of the heart both in the atrial and in the ventricles interpreting the detective events according to certain accepted algorithms and providing stimuli to the chambers as needed to maintain a physiologically appropriate rhythm.

The instant invention has been shown and described herein in what is considered to be the most practical and preferred embodiment. It is recognized, however, that departures may be made therefrom within the scope of the invention and that obvious modifications will occur to a person skilled in the art.

What we claim is:

1. A low profile transvenous electrode system for heart block use in an emergency situation for sequentially pacing both the atrium and ventricle of a human heart rapidly and reliably in a dual chamber mode comprising:
   an external pacemaker including two sequential pulse generators that can provide sensing and stimuli for a ventricle and an atrium;
   a plurality of individually insulated electrical wires bundled together to form at least two separate in-line sets of conductive electrodes, one set for the ventricle chamber and one set for the atrium chamber, said set of atrium conductive electrodes comprising four wires, said set of ventricle conductive electrodes comprising five wires, each set of bundled conductive electrodes forming a single cable-like structure;
   a flexible retaining sheath disposed over said plurality of bundled conductive wires providing a sheath that can be used for insertion of the wire bundles into the heart chambers, said sheath being movable from said wires once inserted into the heart for exposing the wires to the ventricular chamber and the atrium chamber, said sheath being entirely removed from the atrium and ventricle when the transvenous electrode system is engaged;
   each of said wires being configured with a certain resiliency and shape to engage resiliently once released from the sheath against a specific point or area within the ventricle chamber and within the atrium chamber providing a plurality of electrodes disposed within each chamber, each of said ventricular electrodes connected to a ventricular sensor or stimulator in said external pacemaker and said plurality of atrium conductors connected to an atrium sensor or stimulator in said external pacemaker; and
   wherein said separate in-line sets of conductive electrodes being configured to pace and sense both atrial and ventricular chambers and provide dual chamber control of the heart.

2. A system as in claim 1, including:
   each of said wires being pre-shaped with the proper orientation and resiliency so that as the sheath is pulled back each wire moves outwardly until the wire tips rest against the interior wall of each of both the ventricular and atrium chamber.

3. A device as in claim 1, wherein:
   each of said wire electrodes includes a blunt ball conductive tip ending connected to each wire for contact with the ventricle and atrium chamber walls providing electrical stimuli to the ventricular and atrium walls.

4. A system as in claim 1, wherein:
   each conductive wire contained within such system is dedicated to either (i) the conduction of electronic stimulation from the pacemaker to myocardial tissue, or (ii) the conduction of electronic information from myocardial tissue to the pacemaker.

5. A device as in claim 1, wherein:
   each of said wires is comprised of a shape memory material with superelastic properties, such as Nitinol™ or a similar material.

* * * * *